United States Patent [19]

Falk

[11] 4,112,769
[45] Sep. 12, 1978

[54] MOLTEN METAL DIP SAMPLER

[76] Inventor: Richard A. Falk, 519 Westminster Dr., Waukesha, Wis. 53186

[21] Appl. No.: 808,850

[22] Filed: Jun. 22, 1977

[51] Int. Cl.² .............................................. G01N 1/12
[52] U.S. Cl. .............................................. 73/425.4 R
[58] Field of Search .................. 73/425.4 R, DIG. 9

[56] References Cited

U.S. PATENT DOCUMENTS 3,481,201  12/1969  Falk ................................ 73/425.4 R
3,686,949  8/1972  Hackett ........................... 73/425.4 R Primary Examiner—S. Clement Swisher
Attorney, Agent, or Firm—Wheeler, Morsell, House & Fuller

[57] ABSTRACT

A molten metal dip sampler or ladle comprises a cylindrical refractory sample cup which is manipulated by a handle which is held in embracing relationship with the sample cup by a paperboard sleeve. A bent portion on the handle extends beneath the bottom of the sample cup to support the mold on the handle.

2 Claims, 3 Drawing Figures

U.S. Patent       Sept. 12, 1978       4,112,769
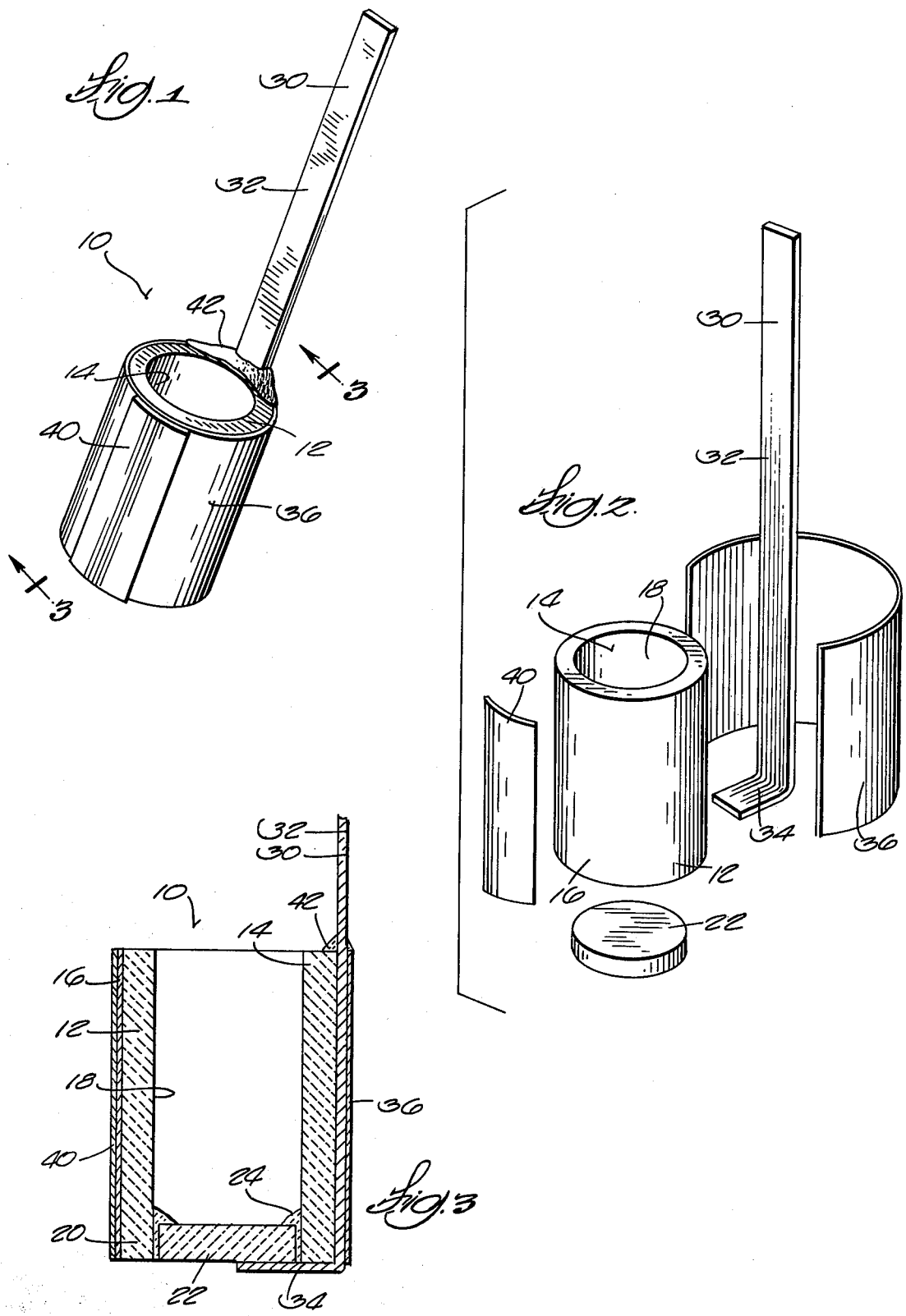

MOLTEN METAL DIP SAMPLER

BACKGROUND OF INVENTION

Small ladles are employed to dip samples from ingot molds and other slag free melts. Some prior art sampling ladles include a small metal cup with a steel handle integrally secured to the cup. In the preferred form the cup is coated with a release agent to prevent skulling and insure easy sample release. Ladles of this type are intended for repetitive use and are returned to the supplier for cleaning and recoating with the release agent. The invention provides a disposable ladle which employs a refractory cup with a paperboard sleeve which prevents skulling. The sample is easily retrieved by fracturing the refractory cup.

SUMMARY OF THE INVENTION

A molten metal dip sampler or ladle for use with any source of hot metal, and particularly ingot molds and other slag free melts, includes a cylindrical refractory mold or cup for forming a cylindrical shaped specimen which is easily sliced for spectrographic analysis. The bottom of the cylindrical refractory mold is sealed by a circular disc which forms the bottom wall for the sample cavity. The sample mold is manipulated with a steel handle which is secured to the exterior surface of the sample mold by a split paperboard sleeve which encapsulates both the mold and a portion of the handle. After assembly the edges of the sleeve can be secured by tape. A bent portion on the handle rests beneath a sample mold bottom wall to prevent loss of the mold from the handle during use.

The sampler provides a sample shape which is suitable for slicing for analysis without preliminary shaping or smoothing of the sample surface. The sample mold is easily fractured to recover the sample.

Further objects, advantages and features of the invention will become apparent from the disclosure hereof.

DESCRIPTION OF THE DRAWINGS

FIG. 1 is a perspective view of a sampler in accordance with the invention.

FIG. 2 is an exploded perspective view of the sampler shown in FIG. 1.

FIG. 3 is an enlarged sectional view along lines 3—3 of FIG. 1.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows a dip sampler or ladle which is preferably used for taking a sample from any source of slag free molten metal. In the disclosed construction the sampler 10 has a continuous cylindrical wall 12 constructed of refractory material. The wall 12 defines a cylindrical mold cavity 14 which is desirably of a diameter so that slices of the cylinder are a suitable size for spectrographic analysis. The wall 12 has an exterior surface 16, an interior surface 18, and an end surface 20.

The bottom of the mold cavity is sealed by a refractory disc 22 which is sized to interfit within the inside of the wall 12. The bottom disc 22 is secured to the inside surface 18 by refractory cement 24.

A handle 30 is provided for manipulating the sampler during use. The handle 30 has an elongated portion 32 and an inturned portion 34. Means are provided for preventing skull formation on the mold walls and for securing the handle to the cylindrical wall 12. In the disclosed construction the means includes a split paperboard sleeve 36 which is sized to fit around the handle 30 and wall 12 to hold the handle 32 in embracing contact with the wall 12. As shown in FIG. 3, the inturned portion 34 abuts the lower edge 20 of the refractory wall and extends inwardly beyond the inside surface 18 to support the disc 22 and cylindrical wall 12. The inturned portion prevents separation of the handle from the mold. The paperboard sleeve 36 can be split longitudinally to facilitate assembly. The adjacent longitudinal edges of the sleeve 36 are then secured together by tape 40 or glue. The sleeve 36 can be secured to the handle and wall 12 by refractory cement 42. An ablative cement coating could alternatively be employed for securing the handle to the mold and to prevent skull formation.

The invention provides a disposable dip sampler or ladle which provides good sample release and is inexpensive to manufacture.

What I claim is:

1. A molten metal dip sampler comprising a refractory cup having wall means having an exterior surface and an interior surface and an end surface, said wall means defining a sample cavity, a refractory bottom wall for said cup providing a bottom for said sample cavity, a metal handle for manipulating said sampler, said handle comprising a relatively thin elongated handle portion and an inturned portion and paperboard sleeve skull preventing means on said exterior surface of said wall means to prevent skull formation on said wall and for securing said elongated handle portion in abutting contact along the entire length of said exterior surface of said cup and said inturned portion extending beneath a refractory bottom wall to support said refractory cup on said inturned portion.

2. A molten metal dip sampler comprising wall means having an exterior surface and an interior surface and an end surface, said wall means defining a sample cavity, a bottom wall providing a bottom for said sample cavity, a handle for manipulating said sampler, said handle comprising an elongated portion and skull preventing means on said exterior surface of said wall means to prevent skull formation on said wall and for securing said handle to said wall means, and wherein said sleeve has a longitudinal split line and tape securing the sleeve together along the split line.

* * * * *